United States Patent [19]

Turner

[11] Patent Number: 4,531,942
[45] Date of Patent: Jul. 30, 1985

[54] IV SECURING MEANS

[76] Inventor: Namon L. Turner, 602 Forest Grove Ave., Jacksonville, N.C. 28540

[21] Appl. No.: 593,545

[22] Filed: Mar. 26, 1984

[51] Int. Cl.³ .............................................. A61M 25/02
[52] U.S. Cl. .................................... 604/180; 128/133; 128/DIG. 26
[58] Field of Search ................ 604/179, 180; 128/133, 128/DIG. 26

[56] References Cited
U.S. PATENT DOCUMENTS

| 3,722,508 | 3/1973 | Roberts | 128/133 |
| 3,918,446 | 11/1975 | Buttarovoli | 128/133 |
| 4,059,105 | 11/1977 | Cutruzzula et al. | 128/133 |

Primary Examiner—John D. Yasko
Attorney, Agent, or Firm—Mills & Coats

[57] ABSTRACT

This invention is a means for securing an intravenous needle and its related tubing in proper location juxtaposed to the hand of a patient. This securing means is semi-mitten shaped in outline and includes a plurality of adjusting straps so that one size fits many different sized hands.

9 Claims, 4 Drawing Figures

IV SECURING MEANS

FIELD OF INVENTION

This invention relates to medical devices and more particularly to means for securing intravenous or IV means in proper juxtaposed position to an appendage of a patient.

BACKGROUND OF INVENTION

Since the medical arts first began injecting fluids in the veins of patients, there has been a problem of maintaining the intravenous needle and its related tubing in proper position relative to the point at which such needle penetrates the skin of the patient. If not adequately secured, the IV can with little effort be pulled out, or even worse, can be unintentionally ripped from the skin causing excessive hemorrhaging and other undesirable results.

The above is particularly true when a patient is sleeping or is in a semi-conscious condition where movement, although unintentional or involuntary, can cause the IV to become dislocated or completely removed from the patient. This situation is undesirable at best and can in the worst situations be extremely injurious or even fatal.

Although various means for securing venous and arterial catheters, intravenous feeding and drug administering means, and the like have been developed, these have in most instances been limited to leg and arm appendages but have not related to IVs inserted into the hand of the patient.

Even with the development of several different types of appendage catheter and IV securing means, medical science has not widely accepted these but still almost invariably uses tape to secure the IV in place, hopefully adequately enough to prevent unintentional removal thereof.

When skin of the patient is wet from blood or other liquids, tape is useless as an IV securing means. This is a particular problem in disaster or emergency situations. Also if swelling occurs, the securing tape can become very uncomfortable or can even pull loose as a result thereof.

Additionally taping causes a problem in pulling the skin of the patient when it is removed thus causing pain and inconvenience. If the IVs are inserted and removed several times, the skin of the patient can become irritated, even to the point of a rash developing causing the IV to have to be placed in another location.

BRIEF DESCRIPTION OF INVENTION

After much research and study into the above-mentioned problems, the present invention has been developed to provide a tapeless means for securing IV tubes and needles in appropriate positions. This is accomplished with minimum time and effort through the use of an open, semi-mitten type configuration having a plurality of strap means secured thereto to allow infinite adjustments as required. Velcro has been found satisfactory as a securing means for the straps. The device of the present invention is particularly adapted for use in conjunction with appendages such as the hands of the patient and, except for the thumb, it encircles all the fingers of the patient as well as the wrist with additional cross means to make the IV tube lie flat juxtaposed to the skin of the patient in a looped configuration.

The device of the present invention is composed of nonallergenic material thus eliminating the rashes so often associated with the taping of IVs. Further, the securing means of the present invention is readily removed when no longer needed and again does not pull the skin nor hurt the patient during the removal process. It is also liquid impervious and its holding power is not effected by moisture nor swelling.

In view of the above, it is an object of the present invention to provide an IV securing means for the hand of a patient.

Another object of the present invention is to provide an IV securing means which is easily adjustable and readily attached and removed.

Another object of the present invention is to provide an IV securing means which is infinitely adjustable to different size hands.

Another object of the present invention is to provide an IV securing means which is nonallergenic and can be readily sterilized for reuse.

Another object of the present invention is to provide an IV securing means which prevents unintentional removal thus protecting the patient from possible injury or death.

Another object of the present invention is to provide an IV securing means which can be readily attached and detached from the patient and which will not irritate the skin of such patient.

Another object of the present invention is to provide an IV securing means which is uneffected by the presence of moisture or liquids.

Another object of the present invention is to provide an IV securing means which automatically compensates for swelling of appendages without loss of holding effectiveness.

Other objects and advantages of the present invention will become apparent and obvious from a study of the following description and the accompanying drawings which are merely illustrative of the present invention.

DETAILED DESCRIPTION OF INVENTION

Figure 1:
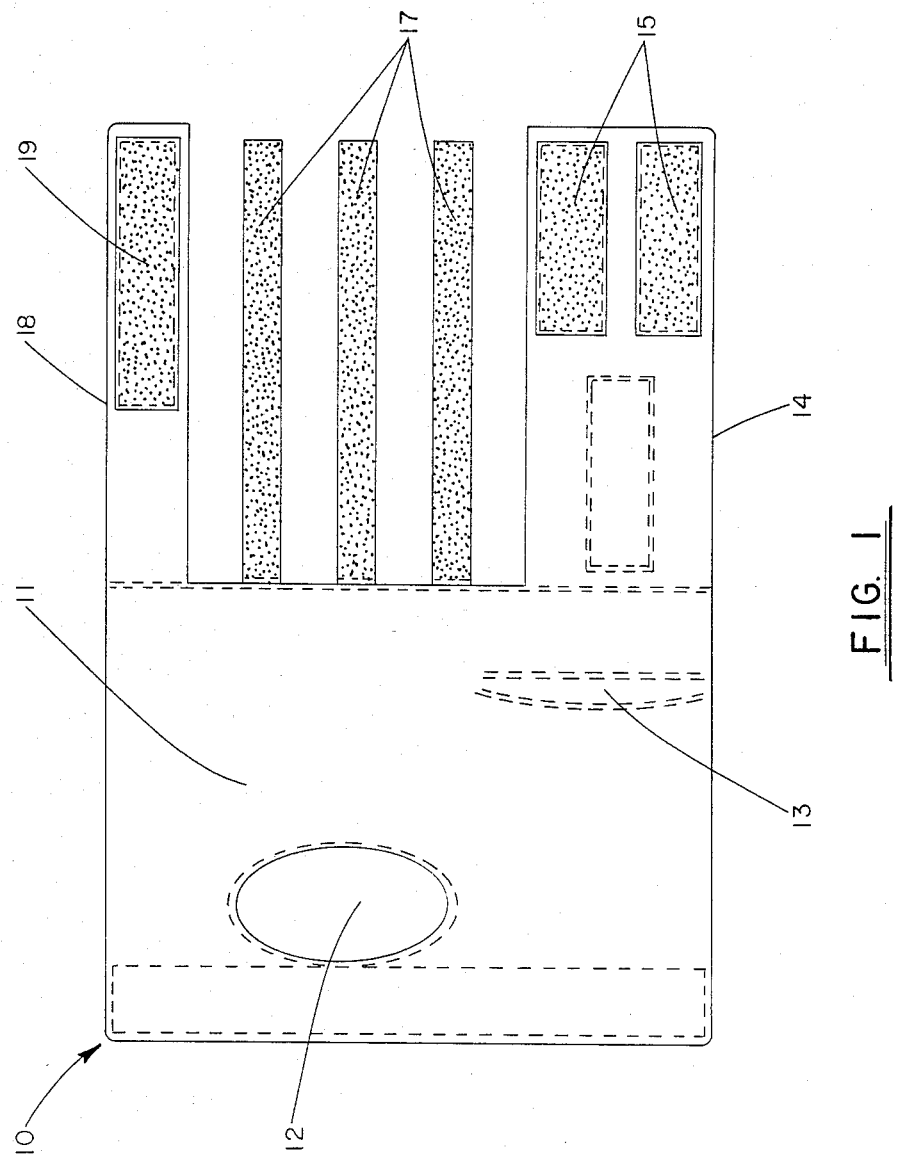
FIG. 1 is a laid out plan view of the interior side of the IV securing means of the present invention.

With further reference to the drawings, the IV securing means of the present invention, indicated generally at 10, includes a palm portion 11 having a thumb opening 12 therein. The palm portion 11 is slightly longer than it is wide and at one end it includes a tuck 13 adjacent a wrist strap 14 which outwardly projects from one side of such portion. This wrist strap has a fibrous loop material 15 stitched or otherwise adhered to a portion of the interior side thereof.

A plurality of IV securing strips 16 are spacingly attached to the same edge of palm portion 11 as wrist strap 14. The interior side of these strips, as shown in FIG. 1, are composed of fibrous loop material 17 similar to the loop material 15 on wrist strap 14.

Extending outwardly from the same edge of palm portion 11 as wrist strap 14 and securing strip 16 is finger strap 18. Stitched or otherwise secured along a substantial portion of the interior of finger strap 18 is a fibrous loop material as can clearly be seen in FIG. 1.

Figure 2:
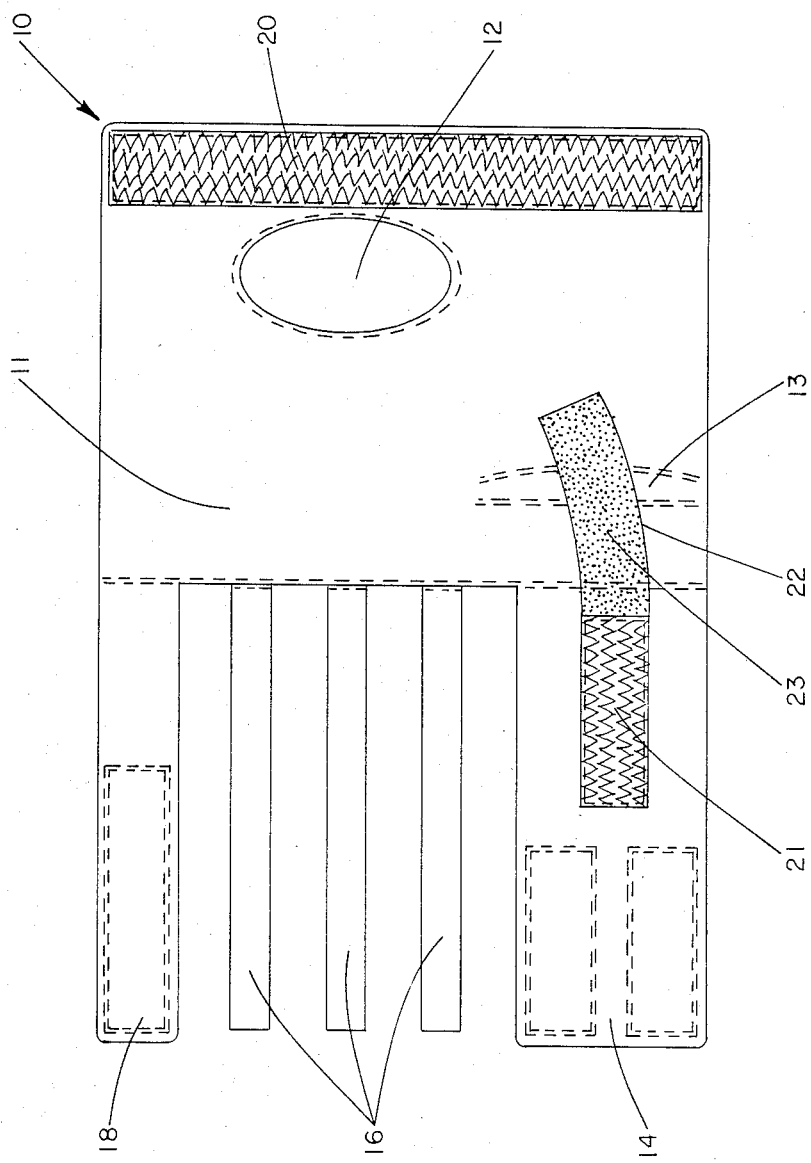
FIG. 2 is a laid out plan view of the exterior side thereof.

Referring now to the laid out exterior plan view of the IV securing means 10 of the present invention as shown in FIG. 2, along the edge of the palm portion 11 opposite the edge having the wrist strap, securing strips and finger strap, and adjacent thumb opening 12, is a hook material 20 which is stitched or otherwise adhered to such portion. This hook material is composed of a multiplicity of small resilient hook means. When the hook material 20 is placed juxtaposed to fibrous loop material and the two are pressed together, the hooks become entangled in the fibrous loops to form a relatively secure and yet releasable bond. This bond is relatively easily broken by peeling the layers apart, however, sliding movement between the surfaces is extremely difficult thereby providing a relatively simple securing means of great strength. Securing products of this type are sold under the brand name Velcro which is readily available commercially.

Figure 3:
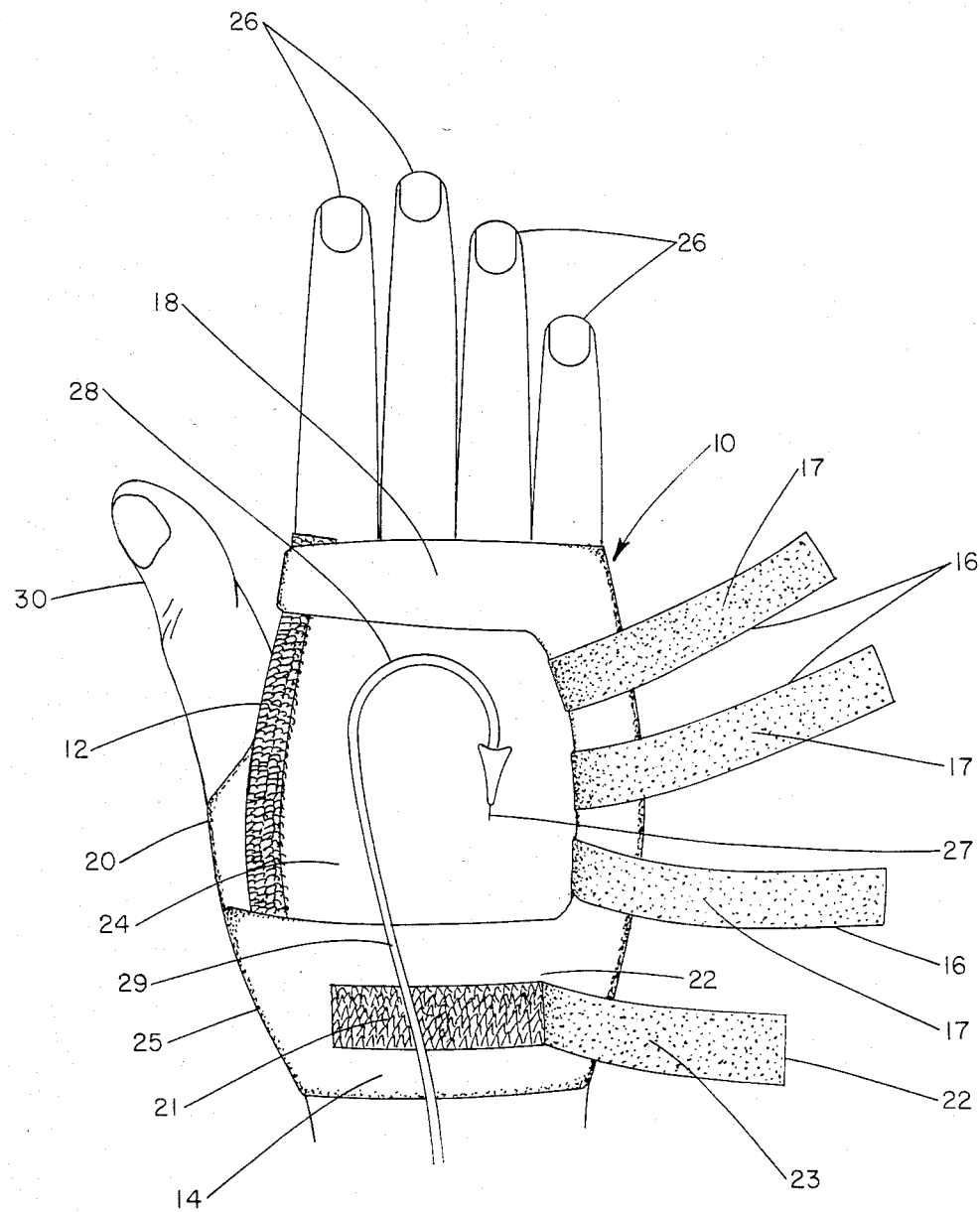
FIG. 3 is a top plan view of the IV securing means ready for use.
Figure 4:
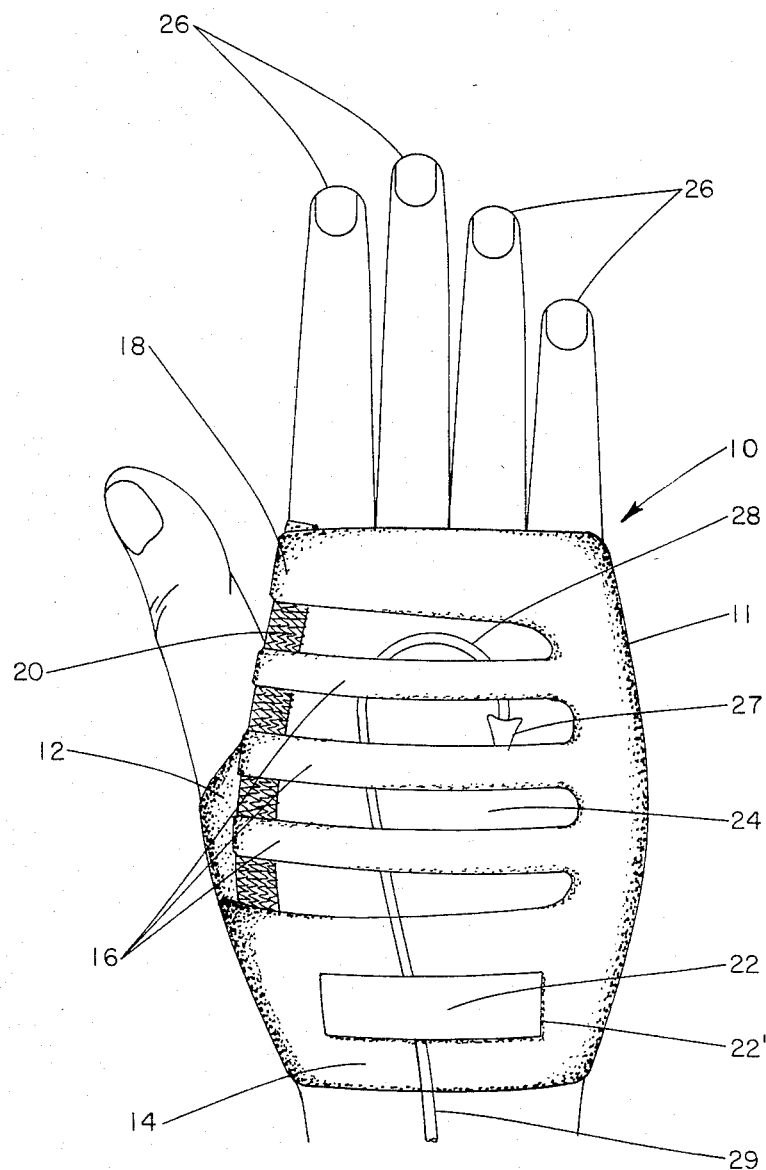
FIG. 4 is a top plan view of the IV securing means in use.

Hook material 21 is stitched or otherwise adhered to the exterior of wrist strap 14 and extends outwardly from where such wrist strap joins palm portion 11. An IV securing strip 22 having a fibrous loop material 23 on one side thereof is stitched or otherwise attached at 22' to one end of hook material 21 in such a manner that it will fold over and lie juxtaposed thereto as shown in FIG. 4 and yet can be peeled back to the position shown in FIG. 3.

The palm portion 11, and if desired, at least a portion of the wrist strap 14 and the finger strap 18 can be composed of an elastic material which allows the tension on the IV securing strips 16 to be adjusted as well as automatically compensating for any swelling that occurs in the hand of the patient without the IV securing means having to be removed or resecured. A washable, non-allergenic material of this type is the elastic bandage material sold under the brand name Spandex which is readily available commercially.

To use the present invention, an appropriate left-handed or right-handed IV securing means is selected and is laid flat under the palm of the hand of the patient with the thumb of such patient passing through thumb opening 12. The wrist strap 14 and the finger strap 18 are pulled across the top of the wrist 25 and fingers 26, respectively, of the hand 24 of the patient with the fibrous loop material 15 of wrist strap 14 and the fibrous loop material 19 of finger strap 18 both being pressed against the hook material 20 thus securing such straps in the position shown in FIG. 3.

Next an IV needle 27 is inserted into a vein on the top of the hand 24 of the patient in the normal manner. A loop 28 is then formed in the IV tube 29 associated with needle 27 as illustrated in FIG. 3.

The IV securing strips 16 are then pulled over the IV needle and tube and when proper tension is achieved, the fibrous loop material 17 is pressed against hook material 20 to secure the strips in place. Finally IV securing strip 22 on wrist strap 14 is pulled over and pressed down against hook material 21 to firmly secure the IV tube 29 as is clearly shown in FIG. 1.

Should the IV tube 29 and/or its associated needle 27 need to be checked and/or adjusted, all that is necessary is for the IV securing straps 16 to be peeled back from hook material 20 and then repositioned.

Whenever it is desired to remove the IV securing means 20 of the present invention, the IV securing straps 16 and 22 are peeled back and the IV needle and tube removed from the hand 24 of the patient. Then the wrist strap 14 and the finger strap 18 are peeled back from hook material 20 and the palm portion 11 slid off the thumb 30 of the patient. Since material from which the IV securing means 10 of the present invention is constructed is non-allergenic and does not stick to the skin of the patient, no rash or other reaction will occur.

From the above it can be seen that the present invention has the advantage of being relatively inexpensive to manufacture and sell while at the same time being a superior IV securing means in that it is non-allergenic, can be removed and replaced as often as necessary, is non-affected by moisture and liquids, and can automatically compensate for swelling as it occurs.

The present invention can, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A means for holding an IV type means in place juxtaposed to the hand of a patient comprising: a palm portion; a wrist strap means extending from one edge of said palm portion, across the wrist of the patient, and releasably secured to the opposite edge of said portion; a finger strap means extending from one edge of said palm portion, across the fingers of the patient, and releasably secured to the opposite edge of said portion; and at least one IV holding strip means extending from one edge of said palm portion, across the hand of the patient, and releasably secured to the opposite edge of said portion whereby an improved, non-adhesive means is provided for securing an IV in place juxtaposed to the hand of the patient.

2. The holding means of claim 1 wherein a plurality of IV holding strips extend from one edge of said palm portion, across the hand of the patient, and releasably secured to the opposite edge of said portion.

3. The holding means of claim 3 wherein an IV holding strip is provided on said wrist strap means whereby additional holding power for the IV is provided.

4. The holding means of claim 1 wherein the wrist strap securing means is a loop and hook type fastening material.

5. The holding means of claim 1 wherein the finger strap securing means is a loop and hook type fastening material.

6. The holding means of claim 1 wherein the IV holding strip securing means is a loop and hook type fastening material.

7. The holding means of claim 1 wherein said palm portion is formed from an elastic type material.

8. The holding means of claim 1 wherein the holding ability of the wrist and finger strap means and the IV holding strip are not affected by moisture or liquid.

9. The means of claim 1 wherein said holding means is constructed from non-allergenic materials.

* * * * *